United States Patent [19]

Mulqueen et al.

[11] Patent Number: 5,436,223
[45] Date of Patent: Jul. 25, 1995

[54] ARGRICULTURAL FORMULATIONS COMPRISING FLUROXYPYR ESTERS WHICH ARE LIQUID AT 25° C.

[75] Inventors: Patrick J. Mulqueen, Abington; Graham Banks, Uffington; John Davies, Watlington; Eileen A. Paterson, Grove; Marten Snel, Wantage, all of United Kingdom

[73] Assignee: DowElanco, Indianapolis, Ind.

[21] Appl. No.: 233,207

[22] Filed: Apr. 26, 1994

Related U.S. Application Data

[63] Continuation of Ser. No. 52,446, Apr. 23, 1993, Pat. No. 5,374,603.

[51] Int. Cl.$^6$ .................. A01N 43/653; A01N 43/40; A01N 43/90; A01N 33/22
[52] U.S. Cl. ...................... 504/128; 504/130; 504/135; 504/136; 504/139; 504/255
[58] Field of Search ............... 504/130, 255, 128, 135, 504/136, 139

[56] References Cited

U.S. PATENT DOCUMENTS 4,108,629  8/1978  McKendry ............... 71/94

FOREIGN PATENT DOCUMENTS 441457  8/1981  European Pat. Off. .
381691  10/1992  European Pat. Off. .
512684  11/1992  European Pat. Off. .
67712  12/1992  European Pat. Off. .
67713  12/1992  European Pat. Off. .

Primary Examiner—S. Mark Clardy
Attorney, Agent, or Firm—D. Wendell Osborne

[57] ABSTRACT

Agricultural formulations of fluroxypyr that contain an ester of fluroxypyr that is liquid at ambient temperatures, such as the 1-butoxy-2-propyl ester or the 2-ethylhexyl ester, and that contain a reduced amount of organic solvent or no organic solvent are disclosed. The formulations have good physical properties and are highly effective herbicides.

12 Claims, No Drawings

ARGRICULTURAL FORMULATIONS COMPRISING FLUROXYPYR ESTERS WHICH ARE LIQUID AT 25° C.

This is a continuation of application Ser. No. 08/052,446 filed Apr. 23, 1993, now U.S. Pat. No. 5,374,603.

BACKGROUND OF THE INVENTION

Agricultural chemicals, such as herbicides, insecticides, and fungicides are typically coined with carriers and adjuvants to obtain a formulated product before sale to the ultimate user. The adjuvants and carriers employed add to the cost and, in some cases, make the products less desirable environmentally. On the other hand, these ingredients often contribute positively to the efficacy of the formulated product. The organic solvents, especially hydrocarbon solvents, typically found in formulated agricultural products are examples of carriers that have these characteristics. The preparation of formulated agricultural products that contain very little or no organic solvent, and, especially, no petroleum hydrocarbon or chlorinated hydrocarbon solvents, but that are at least as effective as formulated products that do, is a desirable objective.

Fluroxypyr, which is ((4-amino-3,5-dichloro-6-fluoro-2-pyridinyl)oxy) acetic acid, is a commercially available herbicide that is presently sold as the 1-methylheptyl ester in the form of an emulsifiable concentrate formulation containing 180 grams of acid equivalent per liter of formulation. Emulsifiable concentrate formulations containing higher levels of this ester and common solvents were found to be unsuitable due to solubility limitations. U.S. Pat. No. 4,108,629 proposes that emulsifiable concentrate formulations containing from about 2 to about 50 percent of fluroxypyr esters can be prepared, but only discloses such formulations containing up to about 25 percent.

Wettable powder and water dispersible granule formulations containing fluroxypyr in the form of the 1-methyl-heptyl ester have not been commercialized because they are not as effective as liquid formulations. The efficacy of such formulations can be improved by the addition of a low-volatile organic solvent, but this is not desirable because, in addition to the previously mentioned disadvantages of such solvents, they reduce the amount of fluroxypyr ester that the product can contain and still maintain acceptable physical properties.

SUMMARY OF THE INVENTION

It has now been found that both liquid and solid agricultural formulations of fluroxypyr that contain a reduced amount or no organic solvent but that have good physical properties and are highly effective can be prepared if one employs as the active ingredient an ester of fluroxypyr that is liquid at ambient temperature. Such esters have melting points below 25° C. and are referred to herein as liquid esters.

The improved agricultural formulations of the invention include emulsifiable concentrate, concentrated aqueous emulsion, wettable powder, and water dispersible granule agricultural formulations containing fluroxypyr wherein the fluroxypyr is in the form of an ester that is a liquid at 25° C., optionally in combination with one or more other compatible herbicides. It especially relates to such emulsifiable concentrate formulations that contain at least 40 weight percent fluroxypyr ester, concentrated aqueous emulsion formulations that contain at least 50 percent fluroxypyr ester in the emulsified phase, and wettable powder and water dispersible granule formulations that contain no organic solvent The improved agricultural formulations of the invention are employed in an improved method of controlling undesirable vegetation with fluroxypyr which method comprises contacting the undesirable vegetation with a spray solution prepared by diluting with water an agricultural formulation of fluroxypyr that contains fluroxypyr in the form of an ester that is a liquid at 25° C., optionally in combination with one or more other compatible herbicides.

The preferred liquid esters of fluroxypyr include the 1-butoxy-2-propyl ester, the 1-butoxy-2-butyl esther, and the 2-ethylhexyl ester.

DETAILED DESCRIPTION OF THE INVENTION

The formulated agricultural products of the present invention are characterized by containing an ester of fluroxypyr that is liquid at 25° C. Suitable esters include the 1-butoxy-2-propyl, 1-butoxy-2-butyl, 1-(1-methoxy-2-propoxy)-2-propyl, 1-(1-butoxy-2-propoxy)-2-propyl, 1-(1-(1-methoxy-2-propoxy)-2-propoxy)-2-propyl, 1-(1-(1-butoxy-2-propoxy)-2-propoxy)-2-propyl, and 2-ethylhexyl esters. These esters are prepared from the following alcohols: 1-butoxy-2-propanol (1,2-propylene glycol monobutyl ether, Dowanol TM PnB), 1-butoxy-2-butanol (1,2-butylene glycol monobutyl ether, Dowanol TM BnB), 1-(1-methoxy-2-propoxy)-2-propanol (dipropylene glycol monomethyl ether, Dowanol TM DPM), 1-(1-butoxy-2-propoxy)-2-propanol (dipropylene glycol monobutyl ether, Dowanol TM DPnB), 1-(1-(1-methoxy-2-propoxy)-2-propoxy)-2-propanol (tripropylene glycol monomethyl ether, Dowanol TM TPM), 1-(1-(1-butoxy-2-propoxy)-2-propoxy)- 2-propanol (tripropylene glycol monobutyl ether, Dowanol TM TPnB), and 2-ethylhexanol.

None of these esters, except the 2-ethylhexyl ester which melts at 19° C., could be made to crystallize when cooled to below 0° C. The 1-butoxy-2-propyl, 1-butoxy-2-butyl, and 2-ethylhexyl esters are typically preferred.

The formulations of the present invention are improved compositions as compared with previously known products because they reduce the amount of or eliminate organic solvents that are environmentally undesirable, they are more concentrated and, therefore, more economically shipped and stored, they are usually more efficacious, and they make it possible to prepare stable combination products with other herbicides.

The esters of fluroxypyr of this invention can be prepared readily by methods well-known in the art, including the method described in published European Application No. 441457, which involves the preparation of the methyl or ethyl ester by alkylation of a salt of 4-amino-3,5-dichloro-6-fluoro-2-pyridinol with methyl or ethyl chloroacetate and subsequent transesterification with the desired alcohol.

The emulsifiable concentrate formulations of the present invention include all such formulation is containing at least 40 percent of a liquid ester of fluroxypyr. Emulsifiable concentrate formulations. containing at least 50 percent are preferred and those containing at least 65 percent are more preferred. These formulations are, further, generally characterized by containing no more than about 55 percent solvent, preferably, no more than about 45 percent solvent, and more preferably, no more than about 30 percent solvent. Emulsifiable concentrate formulations containing no added solvent can be prepared and are included as part of the invention.

The solvents that can be employed in the emulsifiable concentrate formulations of the invention include all agriculturally acceptable solvents in which the active ingredient esters are appreciably soluble. These include xylene-range petroleum solvents ( such as Solvesso TM 100 or 150), naphthalene-range petroleum solvents (such as solvesso TM 200), vegetable oils (such as canola oil, soybean oil, and cotton oil), vegetable oil derivatives (such as methyl oleate and methyl laurate), glycol ethers (such as propylene glycol monobutyl ether (Dowanol TM PnB) and dipropyiene glycol monomethyl ether (Dowanol TM DPM)), and glycol diethers (such as dipropylene glycol dimethyl ether (Proglyde TM DMM) and dipropylene glycol methyl butyl ether (Proglyde TM DMB)), cyclohexanone, N-methyl-2-pyrrolidinone, and the like. An agriculturally acceptable solvent is a solvent that meets the requirements for use in agricultural products in at least one country.

The emulsifiable concentrate formulations of the present invention, which are sometimes referred to as EC formulations, require the presence of one or more surface active agents that cause the solution to form an emulsion on dilution with water. Any agriculturally acceptable surface active agent or combination of surface active agents that is effective in producing a satisfactory emulsion can be employed. Examples of surface active agents that can be employed for one or more of the liquid esters of the invention include salts of alkyl sulfates (such as diethanolamine salts of octadecyl sulfonate), salts of alkylarylsulfonic acids (such as calcium dodecylbenzenesulfonate), alkylphenol-alkylene oxide addition products (such as nonylphenol-$C_{18}$-ethoxylate), alcohol-alkylene oxide addition products (such as tridecyl alcohol-$C_{16}$-ethoxylate), dialkyl esters of sulfosuccinic acid (such as sodium di-2-ethylhexyl sulfosuccinate), sorbitol esters (such as sorbitol oleate), polyalkylene esters of fatty acids (such as polyethylene glycol stearate), block copolymers of ethylene oxide and propylene oxide and salts of mono and dialkyl phosphate esters (such as potassium di-2-ethylhexyl phosphate). Some specific examples include alkali metal dialkyl sulfosuccinates sold under the name Anonaid TM, block copolymers of ethylene oxide and propylene oxide sold under the names Pluronic TM and Atlox TM, graft copolymers of acrylic acid and polyalkytene oxides sold under the name Atlox TM, and fatty alcohol ethoxylates sold under the name Atlox TM. Blends of ionic and non-ionic surfactants are generally preferred. Some specific examples include blends of calcium dodecylbenzenesulfonate and block copolymers of ethylene oxide and propylene. oxide sold under many names, including Atlox TM and Tensiofix TM. An agriculturally acceptable surface active agent is a surface active agent that meets the requirements for use in agricultural products in at least one country.

Surface active agents are typically present in emulsifiable concentrate formulations in concentrations of about 1 to about 20 percent.

The emulsifiable concentrate formulations of the present invention may, optionally, contain other agriculturally acceptable adjuvants commonly used in formulated agricultural products, such as antifoam agents, compatibilizing agents, sequestering agents, neutralizing agents and buffers, corrosion inhibitors, dyes, odorants, penetration aids, spreading agents, dispersing agents, thickening agents, freeze point depressants, antiicrobial agents, crop oil, and the like.

The concentrated aqueous emulsion formulations of the present invention, which are sometimes referred to as EW formulations, include all such formulations containing at least 50 percent of a liquid ester of fluroxypyr in the emulsified phase. Concentrated aqueous emulsion formulations containing at least 65 percent fluroxypyr ester in the emulsified phase are preferred, Those containing at least 80 percent are more preferred, and those containing at least 90 percent are typically most preferred. The surface active agent is assumed to be in the emulsified phase for the purpose of this calculation. These formulations are, further, characterized by containing no more than about 45 percent solvent, preferably, no more than about 30 percent solvent, more preferably, no more than about 15 percent solvent, and generally most preferably no more than about 5 percent solvent in the emulsified phase. In many circumstances it is preferable to have no added solvent in the emulsified phase. Any agriculturally acceptable solvent that is immiscible with water and in which the active ingredient esters are appreciably soluble can be employed. The solvents noted herein to be suitable for emulsifiable concentrates are also generally suitable for concentrated aqueous emulsions.

Concentrated aqueous emulsion formulations require the presence one or more surface active agents that are capable of creating a storage-stable concentrated emulsion and are further capable of creating a dilute emulsion on dilution with water. Any agriculturally acceptable surface active agent or combination of surface active agents that is effective in producing the required emulsion performance can be employed. Suitable surface active agents are of the types noted to be useful for emulsifiable concentrates. Block copolymers of ethylene oxide and propylene oxide are often preferred. Concentrations of surface active agents of about 0.05 to about 10 percent by weight of the total formulation are typical.

Concentrated aqueous emulsion formulations, by definition, require the presence of an aqueous medium as the continuous phase. Sufficient aqueous phase must be present to permit the formation of a storage-stable oil-in-water emulsion. Weight percentages of emulsified organic phase in the finished formulated products of the present invention of up to about 80 percent are possible, weight percentages below about 70 percent are preferred, and weight percentages between about 20 percent and about 60 percent are often more preferred.

The aqueous medium of concentrated aqueous emulsion formulations typically contains a freeze-point depressant, such as propylene glycol, ethanol, propanol, ethylene glycol, glycerol, urea, and ammonium chloride. Propylene glycol is often preferred. Any agriculturally acceptable freeze-point depressant that does not destabilize the emulsion or detract from the efficacy of the product, however, can be employed. The aqueous medium also, typically, contains a thickening agent to help stabilize the emulsion. Water soluble or water dispersible polymers, such as polyvinyl alcohol, polyvinylpyrrolidone, xanthan gum, guar gum, methyl cellulose, and hydroxymethyl cellulose are generally employed for this purpose. Polyvinyl alcohol is generally preferred. Additional thickening agents, including clays such as bentonite, gums such as Veegum ™, and cellulose derivatives such as Avicel ™, can also be employed.

Concentrated aqueous emulsion formulations may also contain other compatible adjuvants, such as those listed for emulsifiable concentrate formulations.

The wettable powder and water dispersible granule formulated agricultural products of the invention, which are often referred to as WP and WG (or WDG) formulations, respectively, generally contain about 20 to about 80 percent of a liquid ester of fluroxypyr in combination with a finely divided solid carrier, such as a clay or a silica. China clay and precipitated silica, such as that sold under the name Sipernat ™, are typical. Solid formulations of this type containing higher concentrations of liquid fluroxypyr esters are, generally, contraindicated because they tend to agglomerate. Such formulations containing lower concentrations tend to be uneconomical to produce. Concentrations of fluroxypyr ester of about 35 to about 65 percent are generally preferred.

Alternately, wettable powder formulations can be prepared by spray-drying an aqueous emulsion of a liquid ester of fluroxypyr containing a water-soluble polymer, such as polyvinyl alcohol, in the aqueous phase. Water dispersible granules can be obtained by agglomeration of the products obtained. Such products containing 40 to 80 percent fluroxypyr ester are generally preferred.

Wettable powder and water dispersible granule formulated agricultural products require the presence of a surface active agent. Any agriculturally acceptable surface active agent capable of creating a suspension of the solid particles when the product is diluted with water and is compatible with the other components of the formulation can be employed. The surface active agents listed above for emulsifiable concentrates are generally useful. Blends of ionic and non-ionic surfactants on a precipitated silica carrier are often preferred. The surface active agents are generally present to the extent of about 3 to about 20 percent.

Additional adjuvants are often employed in wettable powder and water dispersible granule formulations. Thus, agents that assist in the dispersion of the particles, agents that prevent caking, agents that promote free-flow, and other adjuvants such as those noted above for emulsifiable concentrate formulations may also generally be employed.

The compositions of water dispersible granule formulations are, typically, very similar to those of wettable powder formulations. They are generally prepared by agglomeration of wettable powders by chemical and/or physical means.

The compositions of the present invention are also useful for the preparation of combination products containing, in addition to the liquid ester of fluroxypyr, one or more other compatible herbicides. In this embodiment of the invention, the formulated compositions of the present invention are combined with other compatible herbicides in the form of either technical materials or formulated products to obtain combination formulated products. The presence of a liquid ester of fluroxypyr in formulations containing a mixture of herbicides imparts both chemical and physical stability to the compositions. Further, the presence of a liquid ester of fluroxypyr often significantly reduces the phytotoxicity to desirable crops that is frequently encountered when combination products involving a conventional emulsifiable concentrate of a conventional ester of fluroxypyr are employed. As a result, commercially acceptable herbicide mixture formulations can be prepared that, because of chemical, biochemical, or physical incompatibility, are not possible when conventional esters of fluroxypyr are employed.

An 'other compatible herbicide' is a herbicide which is not a salt or ester of fluroxypyr acid and which, when present in a formulation containing a liquid ester of fluroxypyr, does not have a commercially significant deleterious effect on the chemical or physical properties of the formulation and which does not have a commercially significant deleterious effect on the level of herbicidal activity or the selectivity of herbicidal activity of that liquid ester of fluroxypyr.

Combination products with a wide variety of herbicides are possible, including sulfonamides (such as flumetsulam and metosulam), sulfonylureas (such as chlorsulfuron, metsulfuron-methyl, thifensulfuron, tribenuron, triasulfuron, and amidosulfuron), biphenyl ethers (such as bifenox and flurogtycofen), phenoxyalkanoic acids and esters (such as 2,4-D, MCPA, and MCPP), halogenated phenol esters (such as bromoxynil octanoate and ioxynil heptanoate), ureas (such as isoproturon, chlortoluron, and methabenzthiazuron), triazines (such as cyanazine, atrazine, and terbutryne), aryloxyphenoxypropionate esters (such as fenoxaprop, clodinafop, haloxyfop, diclofop, and fluazafop), bromfenoxim, bentazone, dicamba, diflufenican, flupoxam, clopyralid, triclopyr, glyphosate, and glufosinate. Combination products with metosulam and bifenox are sometimes preferred.

The physical and chemical properties of the herbicide being combined with the formulated products of the present invention generally determines which of the formulation types (emulsifiable concentrate, concentrated aqueous emulsion, wettable powder, or water dispersible granule) should be employed. The concentration of the liquid ester of fluroxypur in such combination products is generally lower than in formulated products wherein it is the sole active ingredient. The total concentration of herbicidal compounds in combination products that re emulsifiable concentrates is typically at least 40 percent, preferably at least 50 percent, and more preferably at least 65 percent. The total concentration of herbicidal compounds in such products that are concentrated aqueous emulsions is typically at least 50 percent of the emulsified phase, preferably at least 65 percent, more preferably at least 80 percent, and most preferably at least 90 percent. Some concentrated aqueous emulsion combination products contain no added solvent in the emulsified phase. The total concentration of herbicidal compounds in such products that are wettable powders or water dispersible granules is typically at least 20 percent and is preferably at least 35 percent.

The concentration of the active ingredient liquid ester of fluroxypyr in the formulations of the present invention can be expressed in many ways. The most straight-forward measure is the weight percentage of the ester in a solid formulation or the weight of ester per unit volume of a liquid formulation. It is, however, usually more useful to state the concentration in terms of the equivalent weight of fluroxypyr acid in the formulation since the acid is ultimately the active ingredient. The fluroxypyr acid equivalent (ae) is calculated by multiplying the weight of the specific fluroxypyr ester employed by the ratio of the molecular weight of fluroxypyr acid (255.0) to the molecular weight of that ester.

The compositions of the present invention are useful for the control and kill of t undesirable vegetation. They are generally diluted with water, optionally containing agriculturally acceptable adjuvants, before application to the undesirable vegetation in order to obtain a spray solution containing an herbicidally effective amount of the ester of fluroxypyr. The diluted agricultural formulations are then applied by convention means well-known to those in the art.

EXAMPLES

Example 1

Preparation of Oil-In-Water Concentrated Emulsion (EW) Formulated Products.

Formulation A-PnB: An aqueous mixture was prepared adding 0.1 g of a propylene oxide-ethylene oxide block co-polymer non-ionic surfactant, 0.1 g of the sodium salt of a dialkyl sulfosuccinic acid surfactant, 0.1 g of polyvinyl alcohol suspending agent, and 0.3 g of propylene glycol freeze point depressant to 5.4 g of water and to this was added, with high shear mixing, 5.3 g of about 98 percent purity 1-butoxy-2-propyl ((4-amino-3,5-dichloro-6-fluoro-2-pyridinyl)oxy)acetate. Ten mL of a fine droplet-size stable emulsion which had a specific gravity of 1.13 and contained 360 grams of fluroxypyr acid equivalent per liter was obtained.

Formulation A-EH: The procedure described ]for Formulation. A-PnB was followed except that 2-ethylhexyl ((4-amino-3,5-dichloro-6-fluoro-2-pyridinyl)oxy)acetate was the ester added. Ten mL of a fine droplet-size stable emulsion which had a specific gravity of 1.13 and contained 360 grams of fluroxypyr acid equivalent per liter was obtained.

Formulation A-BnB: The procedure described for Formulation A-PnB was followed except that 5.5 g of about 98 percent purity 1-butoxy-2-propyl ((4-amino-3,5-dichloro-6-fluoro-2-pyridinyl)oxy)acetate was the ester added and 5.6 g of water, but no propylene glycol was used. Ten mL of a fine droplet-size stable emulsion which had a specific gravity of 1.14 and contained 360 grams of fluroxypyr acid equivalent per liter was obtained.

Formulation B-EH: A mixture containing (by weight) 290 parts of water, 60 parts of a fatty alcohol ethoxylate surfactant, and 50 parts of propylene glycol freeze point depressant was prepared and to this was added, with high shear mixing, a mixture containing (by weight) 200 parts of methyl oleate, and 520 parts of 2-ethylhexyl ((4-amino-3,5-dichloro-6-fluoro-2-pyridinyl)oxy)acetate. A stable emulsion that had a specific gravity of 1.12 and contained 360 grams of fluroxypyr acid equivalent per liter was obtained.

Example 2

Preparation of Emulsifiable Concentrate EC Formulated Products.

Formulation C-EH: Methyl laurate (450 parts by weight) was placed in a vessel and to this was added 100 parts by weight of a blend of calcium dodecylbenzenesulfonate ionic surfactant and non-ionic surfactants and 520 parts by weight of 2-ethylhexyl ((4-amino-3,5-dichloro-6-fluoro-2-pyridinyl)oxy)acetate. A clear solution having a specific gravity of 1.07 and containing 360 grams of fluroxypyr acid equivalent per liter was obtained.

Formulation D-PnB: The following ingredients were blended together to form 10 mL of a clear mixture: 8.0 g of about 98 percent purity 1-butoxy-2-propyl ((4-amino-3,5-dichloro-6-fluoro-2-pyridinyl)oxy)acetate, 2.4 g of dipropylene glycol methyl butyl ether solvent, 1.2 g of a blend of calcium dodecylbenzenesulfonate ionic surfactant and non-ionic surfactants. The resulting clear emulsifiable liquid had a specific gravity of 1.16 and contained 540 grams of fluroxypyr acid equivalent per liter.

Formulation D-EH: The procedure for Formulation D-PnB was followed using the following ingredients: 7.6 g of about 98 percent purity 2-ethylhexyl ((4-amino-3,5-dichloro-6-fluoro-2-pyridinyl)oxy)acetate, 2.67 g of dipropylene glycol dimethyl ether solvent, and 1.34 g of surfactant blend. The resulting clear emulsifiable liquid had a specific gravity of 1.16 and contained 540 grams of fluroxypyr acid equivalent per liter.

Formulation E-PnB: A blend of calcium dodecylbenzenesulfonate ionic surfactant and non-ionic surfactants (200 parts by weight) was added to 1040 parts by weight of 1-butoxy-2-propyl ((4-amino-3,5-dichloro-6-fluoro-2-pyridinyl)oxy)acetate with stirring. A viscous solution which had a specific gravity of 1.24 and contained 720 grams of fluroxypyr acid equivalent per liter was obtained.

Formulations F-BnP, F-DPH, F-EH, and F-BnB: The general procedure of Formulation D-EH was employed to prepare EC formulations containing 540 g ae of the 1-butoxy-2-propyl, 1-(1-methoxy-2-propoxy)-2-propyl, 2-ethylhexyl, and 1-butoxy-2-butyl esters, respectively. The surface active agent employed was a blend of calcium dodecylbenzene-sulfonate ionic surfactant and non-ionic surfactants and the solvent was Proglyde DMB (dipropylene glycol dimethyl ether). The compositions of the formulations (to prepare 10 mL of formulation) are given in the following table:

|  | F-BnP | F-DPM | F-EH | F-BnB |
|---|---|---|---|---|
| Weight of Ester (g) | 8.1 | 8.3 | 7.9 | 8.3 |
| Weight of Surfactant (g) | 1.3 | 1.3 | 1.3 | 1.3 |
| Weight of Solvent (g) | 2.2 | 2.0 | 2.4 | 2.0 |

Example 3

Preparation of Wettable Powder WP Formulated Product.

Formulation G-PnB: 1-Butoxy-2-propyl ((4-amino-3,5-dichloro-6-fluoro-2-pyridinyl)oxy)acetate (58.0 g of about 98 percent purity) was heated mildly to improve its pourability and was then combined with 32.0 g of precipitated silica in a high speed chopper/blender. Ten grams of a blend of alkytbenzenesulfonic acid salts, alkyl sulfate salts, and nonylphenol ethoxylate sulfonate salts (anionic surfactants) and nonylphenol ethoxylate (nonionic surfactant) absorbed on precipitated silica was added as a wetter/dispersant and the mixture was blended to obtain a finely divided wettable powder containing 40 weight percent fluroxypyr acid equivalent.

Formulation G-EH: The procedure described for Formulation G-PnB was followed except that the ester employed was 57.5 g of about 98 percent purity 2-ethylhexyl ((4-amino-3,5-dichloro-6-fluoro-2 -pyridinyl)oxy)acetate and only 9.0 g of wetter dispersant and 32.5 g of precipitated silica were used. A wettable powder containing 40 weight percent of fluroxypyr acid equivalent was obtained.

Formulation G-BnB: The procedure described for Formulation G-PnB was followed except that the ester employed was 61.3 g of about 96 percent purity 1-butoxy-2-butyl ((4-amino-3,5-dichloro-6-fluoro-2-pyridinyl)oxy)acetate and only 9.0 g of wetter/dispersant and 29.7 g of precipitated silica were used. A wettable powder containing 40 weight percent of fluroxypyr acid equivalent was obtained.

Formulation G-DMP: The procedure described for Formulation G-PnB was followed except that the ester employed was 61.3 g of about 95 percent purity 1-(1-methoxy-2-propoxy)-2-propyl ((4-amino-3,5-dichloro-6-fluoro-2-pyridinyl)oxy)acetate and only 9.0 g of wetter/dispersant and 29.4 g of precipitated silica were used. A wettable powder containing 40 weight percent of fluroxypyr acid equivalent was obtained.

Formulation H-PnB: A uniform mixture of finely divided China clay (100 parts by weight) and precipitated silica (290 parts by weight) was prepared and to this was added, mixing in a chopper/blender, 520 parts by weight of about 98 percent purity 1-butoxy-2-propyl ((4-amino-3,5-dichloro-6-fluoro-2-pyridinyl)oxy)acetate and then 90 parts by weight of a blend of alkylbenzenesulfonic acid salts, alkyl sulfate salts, and nonylphenol ethoxylate sulfonate salts (anionic surfactants) and nonylphenol ethoxylate (nonionic surfactant) absorbed on precipitated silica. The product was blended to obtain a free-flowing wettable powder containing 36 percent by weight of fluroxypyr acid equivalent.

Example 4

Herbicidal Activity of Formulated Products.

The plants used to evaluate the efficacy of the various formulated fluroxypyr esters were grown under glasshouse conditions conducive to their growth and with sub-plot irrigation. The plant species employed and the stage of their growth at which they were employed for the tests were as follows: Galium eparine, 2–3 whorls (GALAP); Lamium purpureum, 4–8 leaves (LAHPU); Rumex obtusifolius, 2–12 leaves (RUMOB); wherein 'leaves' is defined as expanded true leaves.

Spray solutions were prepared by diluting measured amounts of each formulation to be tested with Letcombe, England tap water to achieve the desired highest concentrations. Spray solutions containing less active ingredient were prepared from these by serial dilution. The plants were sprayed, using an overhead track sprayer equipped with a TeeJet ™ 8003 nozzle under a reservoir pressure of 200 kPa (kiloPascals), with an amount of spray solution equivalent to a total volume of 200 liters per hectare. Five to seven concentrations of spray solutions were employed in each test and untreated controls were prepared for comparison. Five to ten replicates of each treatment were made.

The herbicidal effect of each treatment was determined at 14–21 days or at 21–23 days after treatment using a rating scale of 0 to 100 where 0 represents no effect and 100 represents complete kill. The resulting data was analyzed statistically and a $GR_{80}$ (the concentration required to give 80 percent kill) or $GR_{60}$ (the concentration required to give 60 percent kill) were calculated. The results at one dose rate and a calculated GR value are given in the following tables.

a) Herbicidal Activity of EC Formulations (21 Days After Treatment)

| FLUROXYPYR ESTER | FORMULATION (Example No.) | HERBICIDAL ACTIVITY AT 200 g ae/Ha | | HERBICIDAL ACTIVITY $GR_{80}$ g ae/Ha | |
|---|---|---|---|---|---|
| | | GALAP | LAMPU | GALAP | LAMPU |
| 1-butoxy-2-propyl | 360 g ae/L (D-PnB) | 99 | 97 | 48 | 91 |
| 2-ethylhexyl | 360 g ae/L (D-EH) | 98 | 85 | 40 | 95 |
| 1-methylheptyl* | 180 g/L commercial formulation | 100 | 86 | 40 | 132 | b) Herbicidal Activity of EC Formulations-B (23 Days After Treatment)

| FLUROXYPYR ESTER | FORMULATION (Example No.) | HERBICIDAL ACTIVITY AT 180 g ae/Ha | | HERBICIDAL ACTIVITY $GR_{60}$ g ae/Ha | |
|---|---|---|---|---|---|
| | | GALAP | RUMOB | GALAP | RUMOB |
| 1-butoxy-2-propyl | 540 g ae/L (F-PnB) | 78 | 80 | 52 | 32 |
| 2-ethylhexyl | 540 g ae/L (F-EH) | 87 | 76 | 34 | 20 |
| 1-butoxy-2-butyl | 540 g ae/L (F-BnB) | 78 | 76 | 32 | 32 |
| 1-(1-methoxy-2-propoxy)-2-propyl | 540 g ae/L (F-DPM) | 84 | 78 | 55 | 63 |
| 1-methylheptyl* | 180 g/L commercial formulation | 86 | 80 | 67 | 25 | c) Herbicidal Activity of EW Formulations (14 Days After Treatment)

| FLUROXYPYR ESTER | FORMULATION (Example No.) | HERBICIDAL ACTIVITY AT 180 (#) or 200 g/Ha | | HERBICIDAL ACTIVITY $GR_{60}$ g ae/Ha | |
|---|---|---|---|---|---|
| | | GALAP | RUMOB | GALAP | RUMOB |
| 1-butoxy-2-propyl | 360 g ae/L | 93 | 86 | <25 | 87 |

| | -continued | | | | |
|---|---|---|---|---|---|
| 2-ethylhexyl | (A-PnB) 360 g ae/L (A-EH) | 92 | 93 | 48 | 83 |
| 1-butoxy-2-butyl | 360 g ae/L (A-BnB) | 94# | 87# | 35 | 38 |
| 1-methylheptyl* | 360 g ae/L Aqueous Suspension Concentrate | 78 | 73 | 158 | >400 | d) Herbicidal Activity of WP Formulations (21–23 Days After Treatment)

| FLUROXYPYR ESTER | FORMULATION (Example No.) | HERBICIDAL ACTIVITY AT 180 (#) or 200 g/Ha | | HERBICIDAL ACTIVITY $GR_{60}$ | |
|---|---|---|---|---|---|
| | | GALAP | RUMOB | GALAP | RUMOB |
| 1-butoxy-2-propyl | 40% ae (G-PnB) | 88 | 93 | 44 | 63 |
| 2-ethylhexyl | 40% ae (G-EH) | 83 | 95 | 58 | 52 |
| 1-butoxy-2-butyl | 40% ae (G-BnB) | 84# | 82# | 69 | 38 |
| 1-(1-methoxy-2--propoxy)-2-propyl | 40% ae (G-DPM) | 82# | 75# | 69 | 55 |
| 1-methylheptyl* | 40% ae (G-MH) | 43 | 30 | 347 | 478 |

*Standard for Comparison

What is claimed is:

1. An improved emulsifiable concentrate, concentrated aqueous emulsion, wettable powder, or water dispersible granule agricultural formulation containing fluroxypyr wherein the fluroxypyr is in the form of an ester that is a liquid at 25° C., optionally in combination with one or more other compatible herbicides.

2. A formulation according to claim 1 wherein the liquid ester is selected from the 1-butoxy-2-propyl, 1-butoxy-2-butyl, 1-(1-methoxy-2-propoxy)-2-propyl, 1-(1-butoxy-2-propoxy)-2-propyl, 1-(1-(1-methoxy-2-propoxy)propoxy)-2-propyl, 1-(1-(1-butoxy-2-propoxy)-propoxy)-2-propyl, and 2-ethylhexyl ester.

3. A formulation according to claim 2 wherein the ester is the 1-butoxy-2-propyl ester, the 1-butoxy-2-butyl ester, or the 2-ethylhexyl ester.

4. A formulation according to claim 2 which is an emulsifiable concentrate containing at least 50 percent fluroxypyr ester.

5. A formulation according to claim 4 wherein the emulsifiable concentrate contains at least 65 percent by weight fluroxypyr ester.

6. A formulation according to claim 2 which is a concentrated aqueous emulsion containing at least about 50 percent by weight fluroxypyr ester in the emulsified phase.

7. A formulation according to claim 6 wherein the emulsified phase contains at least 65 percent by weight fluroxypyr ester.

8. A formulation according to claim 7 wherein the emulsified phase contains at least 90 percent by weight fluroxypyr ester.

9. A formulation according to claim 8 wherein the emulsified phase contains no added solvents.

10. A formulation according to claim 2 wherein the formulation is a wettable powder or a water dispersible granule containing no added solvents.

11. A formulation according to claim 2 which contains a one or more other compatible herbicides.

12. A formulation according to claim 11 wherein the other compatible herbicide is metosulam or bifenox.

* * * * *